United States Patent [19]

Grisell

[11] 4,077,253
[45] Mar. 7, 1978

[54] APPARATUS AND METHOD FOR THE IMAGING OF THE INTERNAL STRUCTURE OF A THREE-DIMENSIONAL SOLID AND/OR LIQUID OBJECT

[76] Inventor: Ronald D. Grisell, Physiology Dept. U.T.M.B., Galveston, Tex. 77550

[21] Appl. No.: 573,044

[22] Filed: Apr. 30, 1975

Related U.S. Application Data

[63] Continuation-in-part of Ser. No. 473,812, May 28, 1974, abandoned.

[30] Foreign Application Priority Data

Jun. 1, 1973 Germany ................................ 2328119

[51] Int. Cl.$^2$ ............................................. G01N 29/04
[52] U.S. Cl. ........................................ 73/629; 73/603; 340/5 MP
[58] Field of Search .......... 73/67.5 H, 67.5 R, 67.8 R; 350/3.5; 340/5 MP

[56] References Cited

U.S. PATENT DOCUMENTS

| | | | |
|---|---|---|---|
| 3,599,477 | 8/1971 | Cohen et al. ..................... | 73/67.5 R |
| 3,831,434 | 8/1974 | Greguss ............................ | 73/67.5 H |

*Primary Examiner*—Richard C. Queisser
*Assistant Examiner*—John P. Beauchamp
*Attorney, Agent, or Firm*—Charles E. Pfund

[57] ABSTRACT

A system employing ultrasound for the reconstruction of the absorptivity and refractivity properties of ultrasonic radiation internal to a solid, liquid or partly solid and liquid object, air vacuoles being excluded, in the vase that this radiation is highly scattered (reflected or refracted). The reconstruction consists of a three-dimensional simulation of these acoustic properties in a powder mixture which allows access to absorptivity and refractivity information without disturbance either to itself or to the object which it simulates. The reconstruction method is a multi-stage process in which the absorptivity and refractivity of the object are sampled layer-by-layer and recorded in mirror-image layers in the reconstruction. At each stage of the process, the previously constructed image layers are used as "corrective optics" to decode the highly distorted information from the object into the exact wave front geometry and wave form at the given layer that this wave had in the corresponding, mirror-image layer in the object, except for being inverted with respect to one spatial dimension as a mirror image. The necessary sonic data processing is done with a powder mixture, each particle of which is a microscopic mechanism capable of amplifying, recording, erasing and recalling the acoustic impedance information by means of mechanical flexions and other movements.

11 Claims, 7 Drawing Figures

APPARATUS AND METHOD FOR THE IMAGING OF THE INTERNAL STRUCTURE OF A THREE-DIMENSIONAL SOLID AND/OR LIQUID OBJECT

CROSS REFERENCE TO RELATED APPLICATION

This application is a Continuation-in-Part of my copending application U.S. Ser. No. 473,812, filed on May 28, 1974, now abandoned.

BACKGROUND

The field of application of the invention pertains to the imaging of a solid, liquid or solid/liquid object, which may be highly multiply scattering with respect to the ultrasonic radiation utilized in the imaging process, and which it may be desirable not to disturb or destroy thereby; such as, for example, a living brain.

As to the prior art, holographic and scanning processes find many applications in medicine and industry, (Journal "IEEE Transactions on Sonics and Ultrasonics," volume SU-15, number 3, pages 144 to 146, year 1972) and (Journal "Journal of the Acoustical Society of America," volume 44, number 5, pages 1324 to 1338, year 1968). As one may see in classical treatments, (Book "Progress in Optics," volume 3, chapter 1, publisher, North-Holland, year 1964) the mentioned processes are not capable of reconstruction of the internal structure of an object when the radiation employed is multiply scattered before it reaches the recording device. At the present time, the application of ultrasonic radiation to the visualization of the living brain (Journal "Journal of the Acoustical Society of America," volume 44, number 5, pages 1339 to 1345) is hindered by undesirable echo-effects and unpredictable or uncalculable obstructions, as for example, the skull bone. If the wavelength is made short enough to resolve small groups of neurons and similar tiny structures, these side-effects become totally unmannageable and, in addition, absorption becomes a major difficulty.

SUMMARY

The invention provides a means of reconstructing the internal structure of an object, on the basis of information obtained from ultrasonic pulses repeatedly passing through that object, even when the ultrasound is multiply scattered inside the object. Other methods in the current state of the art employing a single stage of insonification cannot therefore resolve internal structure due to tortuous ray paths and specular reflection. The problem is solved by a multi-step or recursive process whereby previously reconstructed layers in the image are used as "corrective optics" in the construction of a given layer. The image medium contains a homogeneous powder mixture, whose particles are mechanisms of characteristic dimension smaller than a wavelength of the ultrasound employed and which performs the necessary ultrasonic data processing. The end result is an image which has exactly the same absorptivity and refractivity properties as the object, and, in addition, can amplify where the object attenuates, with the same factor. Since the image is geometrically the mirror-image of the object with respect to the plane of the ultrasonic pulse generator, a pulse reflected or transmitted in the object will be amplified in the image medium where it was attenuated in the object, and the mirror-image refractivity will so reconstruct its wave front geometry that it arrives at any given point in the image with exactly the mirror-image amplitude and geometry that it had at the corresponding mirror-image point in the object. This allows a sampling of the pulse properties in the image medium, rather that disturbing the object, by surgical means, for example.

DESCRIPTION OF THE PREFERRED EMBODIMENT

Figure 1:
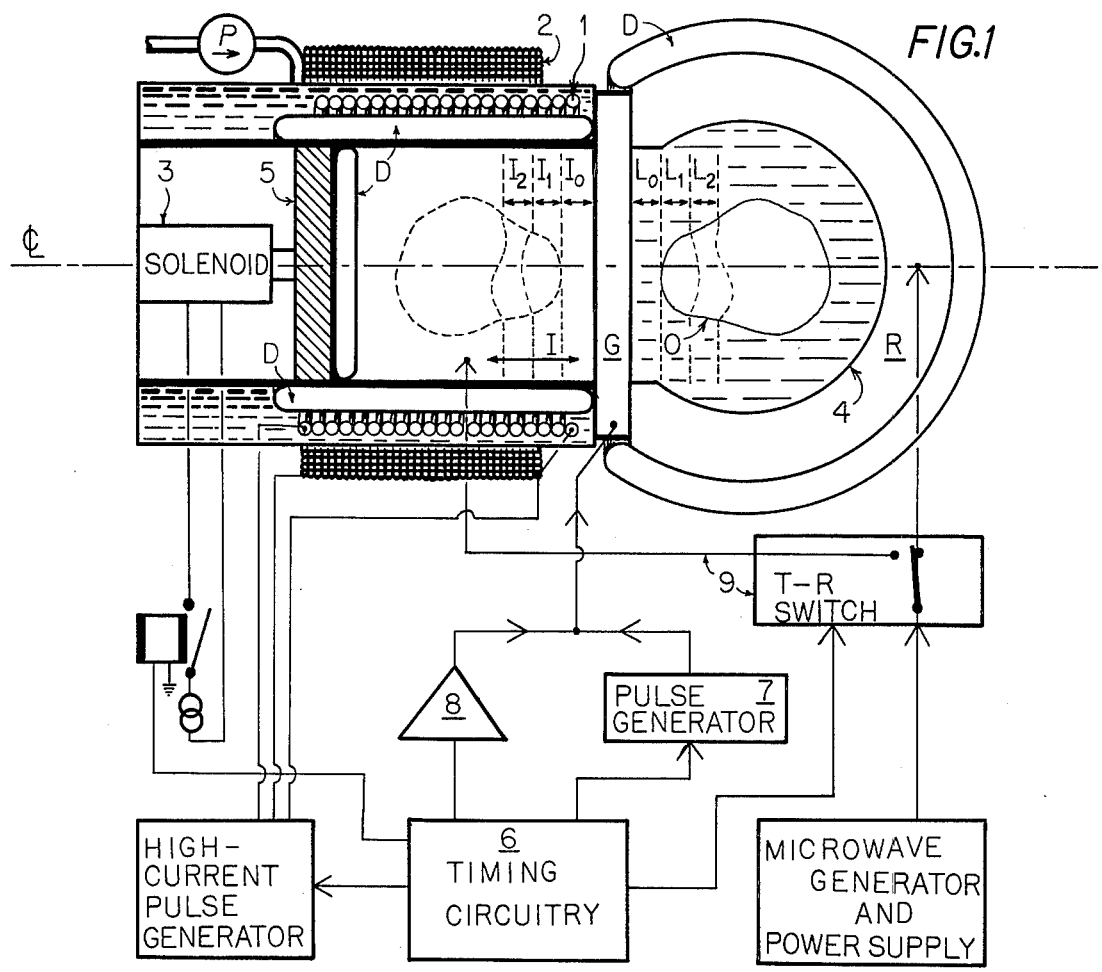
FIG. 1 illustrates the multi-step method whereby each succeeding layer $L_i$ consisting of that region of the object through which a wave front passes between instants of time $(i-1)\Delta T$ and $i\Delta T$, ($i$ being an integer and $\Delta t$ a given interval of time), is reconstructed in a mirror-image layer $I_i$ in the image medium I, by means of information stored in layers $I_1, \ldots, I_{i-1}$. Layer $L_o$ is the whole, homogeneous material or liquid surrounding the object, used as a sound coupling medium, and $I_o$ is the mirror-image region of I with respect to the plane of G (the generator) of $L_o$ in so far as acoustical impedance and geometry near the surface of the object are concerned. Aside from P, 9 and the control circuitry, which are shown only schematically, the apparatus may be designed cylindrically symmetrically about the horizontal center line, hence only a cross section of the apparatus is drawn.

Two types of media, I and R, are required to perform the ultrasonic information processing necessary to carry out the multi-step reconstruction method, each consisting of a certain uniform mixture of powders. The powder particles will first be described, and then the mixture and uses. The first type of particle, hereafter called type aI, is constructed as follows:

1. In pure water, suspend droplets of a 1:1:1-mixture of a room-temperature melting tacky substance or adhesive (e.g. Parafilm "M," product of the American Can Co.), solvent for that substance immiscible in water (e.g. toluene) and fine, magnetic particles (e.g. 4 micron dia. samarium-cobalt particles). This can be done by shaking, or sonication with ultrasound if the droplets are difficult to keep separate. It is better if there are at least 100 magnetic particles per droplet, and the droplets should be less than a quarter wavelength of the ultrasound to be employed in the imaging process.

2. Encapsulate the droplets in RTV (room temperature vulcanizing) rubber. Best results are obtained with the finest (uncured) latexes, with latex particles less than a micron in diameter. The ratio by volume of latex to colloid should be about 1:5, and more than twice as much catalyst as normal is required to vulcanize the rubber in the colloidal suspension as it coats the droplets.

3. Dessicate the coated spherules, removing water as well as internal solvent, thus causing the adhesive-magnet mixture to form a relatively thin coating on the inside of the shell of elastic material. They can be sorted in size by standard floatation techniques. The second type of particle, hereafter called type $nf$, is constructed as in steps 1,2 and 3 above, and in addition: 4. Coat the type $aI$ particles with an approx. 1:1-paste of latex and same magnetic particles, catalyzed, and suspend again in water until vulcanized. Thickness of paste should be twice that of elastic shell.

There are seven basic operations performed by these two types of powder particles, hereafter called micromechanisms, in their processing of acoustic impedance information as they constitute a particular medium in mixtures to be described later.

a. Initial preparation is obtained as follows: Apply a sufficiently high pressure (as much as 3 atmospheres) to micromechanisms of type $aI$, or of type $nf$, as conveyed to them by a liquid vehicle to be described later, so that their shells are compressed into (as in FIG. 3b.) flattened balls. Heat the micromechanisms in this compressed state just above the melting point of their internal adhesive, while applying externally a magnetic field (via coils 1 and 2, FIG. 1) until the magnetic particles in the adhesive line up in contact to form electrically conducting pathways through the adhesive of much greater length than a single particle diameter (thus it can be heated by the RF-field to be described). Cool to tack temperature, and then return pressure to atmospheric. The shells will now be held in their compressed states by the adhesive, which has a highly pressure-senseitive resistivity due to the delicate contacts between magnetic particles, (1, FIG. 3 part c). This resistivity is quite high, since the elastic shells apply a tension to the adhesive which separates most of the conducting magnetic particles slightly. The mechanisms are now ready for activation.

b. Activation consists of applying an electromagnetic, oscillating field of frequency in the microwave range whose electric vector is alternating in a line nearly parallel to the direction of the preparatory magnetic field, although this is not critical. The electromagnetic field, hereafter called RF-field, will heat the prepared adhesive to a temperature just below that where its adhesive strength decreases, the field-strength of which must be determined empirically for a given mixture, as this is a rather sensitive, but not difficult, adjustment. At this stage of activation, micromechanisms of both types *a*I, and *nf*, appear as in FIG. 3 part *c*, with magnetic particles 2 aligned in the adhesive tacking the two sides of flattened shell together.

c. Still under activation by the above-mentioned RF-field above, as a sound wave-crest (pressure maximum) is passing a given micromechanism, the slight over-pressure squeezes the conducting particles 2 into better electrical contact, thus decreasing resistivity in the adhesive considerably. The RF-field then rapidly heats the adhesive further, above its weakening point, and the micromechanism's shell 3 expands as the bonds holding it in its compressed state are broken. With type *a*I, this expansion is so rapid as to be within a quarter-period of the sound vibration; thus these micromechanisms can increase medium pressure in their vicinity in that period, amplifying the passing sound in a manner somewhat analogous to stimulated emission in a laser: the slight over-pressure of a sound wave-crest causes a mechanism to increase pressure locally much more, and in-phase. The statistics of expansion of a population of micromechanisms is such that the increase of pressure is proportional to the stimulating over-pressure. Expansion of type *nf* need not be so rapid, and depends differently on frequency of stimulating sound from type *a*I as follows:

d. While type *a*I expands without the necessity of an externally applied, constant magnetic field, type *nf* requires such a field momentarily to magnetize the particles in its coating (not in type *a*I shell). Magnetization of the type *nf* shell somehow decreases the resonance damping factor (increases the "Q" of the resonance) to such a point for a compressed and activated (as in state *b*) shell that the adhesive is raised above its melting temperature by the small compressions (intensity 1–100 $W/cm^2$) of passing ultrasonic waves used in the imaging process to be described and by the activating RF-field. We are not clear on the theory as to how this effect is obtained. In any case, the probability that type *nf* will expand from its activated state in the presence of ultrasound is inversely decreased by a slight increase of the frequency of that ultrasound above a fixed value $f_o$ (determined by the generator, G) and increased in proportion to stimulating amplitude, with (coil 1, FIG. 1) application of both a stronger magnetic field (500–1000 gauss) and the above mentioned RF-field. Once expanded, type *nf* cannot be returned to state *b* by recompressions employed in other stages (of up to 3 atmospheres) except according to *g*, following, apparently due to its thicker shell and stiffening of the shell around points of bonding (and of greatest flexing) by the hardened adhesive. Therefore, the once expanded shells cannot be sufficiently compressed to re-establish the adhesive bonds.

e. Under a somewhat higher intensity RF-field (to be determined empirically) and without the constant magnetic field, type *nf* will not expand from state *b*. However, under the same conditions, all type *a*I micromechanisms will expand which have once expanded and have been recompressed. Once-expanded shells will be said to be "recording." State *e* will be used to attenuate by type *a*I without recording by either *a*I or *nf*. Absorptivity of a medium depends on the density of expanded type *a*I, as will be seen later.

f. If type *a*I micromechanisms have been recompressed, tacking the previously broken bonds back together (about 2 atmospheres is normal), and are reactivated with the high RF-field momentarily as state *e* and returned to constant value somewhat lower than that used in *e*, then they will impart to their containing medium an (intrinsic) amplification factor per unit travel—time for a subsequent ultrasonic wave at any given point, called "amplification capacity," which is proportional to the fraction unexpanded by any ultrasound recorded earlier, as by *c*. This will be true over a fair dynamic range of linear micromechanism response (under 100 $W/cm^2$ intensity). Amplification is accomplished, in this state, only by type *a*I shells which have not been recorded (expanded by a passing ultrasonic wave as in *c*), because the lower RF-field allows only those unrecorded to expand. The purpose of the lower magnetic field is to keep the magnetic particles aligned in the adhesive even while it is broken in the amplification process as in *c*. Thus the micromechanisms can be recompressed later to the unrecorded state, b, under the RF-field (the oriented particles in the adhesive still make electrical contact when broken bonds are brought back together, and the RF-field can then re-melt the adhesive and mend it). The magnetic field is so low that it hardly has an effect on the resonance of type $nf$ shells as in d (less than 200 gauss, say).

g. Type $aI$ micromechanisms have both temporary and permanent erasure capability, while type $nf$ can only be permanently erased by step a. Type $aI$ are temporarily erased by reducing external pressure to a fraction of an atmosphere, causing them all to expand to their spherical forms (FIG. 3 part d). However, without magnetic field, the bonds have been weakenned, so that recompression will tack, but the higher RF-field of e and f will re-expand those type $aI$ shells once expanded. Permanent erasure is by a.

The above mentioned information, as stored in micromechanisms, can be recalled in the form of an intrinsic acoustic impedance of medium I (absorptivity, amplification capacity and velocity of propagation, or otherwise known, refractivity) for the purpose of processing the ultrasonic waves to be described later, and this impedance is available, either immediately after recording, or after temporary erasure and recall as in step f. Micromechanisms impart impedance to I (or the medium in which they are contained) depending on their state through a liquid vehicle for the micromechanism mixture composing the medium. The acoustic impedance of this liquid vehicle is chosen to match that of compressed type $aI$ micromechanisms and that of compressed type $nf$, also. If type $aI$ shells are in the expanded state (d, FIG. 3) then they will impart an absorptivity to the medium in proportion to their number expanded per unit volume, because they have a much higher density when compressed than when expanded, and thus will scatter ultrasound when expanded due to the difference between their refractivity and that of the liquid. Type $nf$ have bulk modulus of elasticity equal to that of the liquid, when compressed, causing no alteration of velocity; whereas expanded, their modulus is much higher in the presence of the lower magnetic field (as f) causing a decrease in velocity of ultrasound in their vicinity proportional to the number per unit volume expanded. Approximate proportionality is typically maintained over a dynamic range of up to about 100 W/cm$^2$ or until about 1/10-th of the population is expanded. Since the number so expanded is inversely proportional to frequency-increase as in d, the medium will have a velocity of propagation at each point proportional to this recorded frequency-increase divided by recording amplitude.

It should be understood that operating sound intensity levels and operating field strengths must be adjusted to a given batch. With the strengths of activating fields so adjusted and in the recompressed, reactivated state, as above, the micromechanisms originally expanding with the recording process have a greater tendency to expand in proportion to the intensity of a subsequent ultrasonic wave than those unexpanded with recording, probably because the re-established adhesive bonds are weaker than the originally prepared bonds. For the RF-field of f, amplification per unit travel-time which the subsequent wave has will depend proportionally on the intensity of the recorded wave at each of the points of the medium. The explanation has already been given under step c as to how amplification takes place in an unrecorded population of type $aI$ micromechanisms.

Here, with the recorded intensity information and in the recompressed, reactivated state, that is, with the information recalled, the probability of expansion will be proportional to the product of the stimulating wave over-pressure and the recorded intensity. In other words, the recorded intensity can be in proportion to amplification capacity, as in copending application U.S. Ser. No. 473,812.

Image medium I (FIG. 1) thus consists of a 1:1-mixture of micromechanisms of types $aI$ and $nf$ in a liquid vehicle matching the impedances of compressed type $aI$ and compressed type $nf$, so that, an unrecorded image medium has an absorptivity greater than the maximum expected absorptivity in the object to be imaged, thus will be within range of the instrument. Very large compressed absorptivities for type $aI$ can be obtained by making thin shells and using high pressures of preparation and recompression, as well as by making their compressed diameter near a quarter-wave length of the ultrasound used in imaging. Smaller diameters have less scattering power, but greater resolution.

Medium R (FIG. 1) consists entirely of micromechanisms of type $aI$ in a liquid vehicle, to be described subsequently. In particular, R is able to reverse the direction of propagation of any pulse or ultrasonic wave that happens to be passing through the medium at the exact instant it is "activated" by an externally applied field, in this case, an RF-field of sufficiently high intensity that the adhesive in type $aI$ micromechanisms with its magnetic particles aligned as in preparation step a has a temperature just below its melting point, maintained by the heating of the RF-field, as in activation step b. The slight over-pressure of the wave-crests will then trigger the expansion of type AI shells suddenly and in phase with itself, with the resulting production of a larger amplitude wave of the same wave front geometry travelling in the reverse direction. It should be pointed out that both a forward and a reverse or "conjugate" wave are generated thereby from the incoming wave, due to the equidirectional expansion of the type $aI$ shells, but that the forward wave, travelling in the same direction as the incoming wave, is absorbed in damping media (D as in FIG. 1) and thus removed from interfering with the processing of the reverse wave. Such damping media are standard in ultrasonic technology.

In an embodiment employing 1.5 MHz ultrasound, the following parameters were found optimal, but mentioned here only by way of example and as a guide to the implementor, not as restrictions to the application: Micromechanisms of both types had a diameter of 80 microns, with 4 microns SaCo magnetic particles in their parafilm adhesive. Their shells had a thickness of 3-4 microns in case of type $aI$ and 4-8 microns in case of type $nf$. The liquid vehicle employed for both media I and R was propylene glycol, with density adjusted to acoustic transparency of the media by the addition of small amounts of uncured latex particles, also used in the shells of the micromechanisms, of diameter 1-3 microns. However, a wide variety of other relatively inert chemicals proved satisfactory with more or less filler. For example, mineral oil was adjusted with glass "Microballoons" (a product of Emerson & Cumming, Inc.) of diameter 2-4 microns. The RF- or microwave heating apparatus consisted of a magnetron, switched between waveguides leading to media I and R by means of a T-R switch, and operating at 3kMHz. The T-R switch was controlled at the necessary tenths of microsecond switching times by the timing circuitry by means of the two keep-alive electrodes of the T-R tubes (in the respective output guides of the T-junction). The slower variations of microwave intensity for medium I where obtained by varying the supply voltage to the magnetron. Intensity to the conjugator R was sufficiently high that uniform triggering was obtained over the medium, in spite of the fact that the hemispherical cavity is less than ideal for obtaining a uniform distribution of intensity (exact values were not found necessary to measure). Intensities were adjusted for I such that activation was measured to take place within 1 microsecond or so of application. The magnetic field strength had to go as high as 700 gauss temporarily, as obtained with coils 1 of hollow silver tubes, water-cooled both inside and out, and turned on within a microsecond by capacitor discharge and off by a reverse discharge, with standard technique and power supply. The object was a biological preparation immersed in mineral oil (e.g. a rat head as in FIGS. 1, 0). It was effectively shielded from RF by metallic coated mylar film 4 on the inner side of R and by the metallic coatings of G on the end, both of which electrodes presented low impedance to transmitted untrasound. The method of processing the ultrasonic impedance information mentioned above by means of media I and R consists of a multi-step recursive process. To start the recursive process, an initial image layer, $I_o$, (FIG. 1) will be defined as that part of the image medium I which has the mirror-image shape to that of $L_o$, the liquid bath in which the object O is contained (FIG. 1) with respect to the plane of the generator (G in FIG. 1) as mirror. $I_o$ will also have the mirror-image acoustical impedance, namely homogeneous, as nothing has been recorded in the image medium at this stage. In the $i$-th repetition of the following recursive process of the multi-step reconstruction method, it will be assumed at the beginning of the $i$-th repetition that the image layers $I_1, \ldots, I_{i-1}$ have been prepared previously by carrying out the preceding $i-1$ repetitions (hence the term "recursive"). The main principle of this recursion is to use the preceding $i-1$ layers as "corrective optics" and amplifier with amplification factor at each layer equal to the absorptivity (attenuation factor per unit travel-time with a wave) at the mirror-image point of the object with respect to the generator as mirror, and thus to bring the $i$-th testing wave from the object layer $L_i$ to the mirror-image image layer $I_i$ with wave-front geometry and amplitude the mirror-image of what it had in $L_i$. It follows that the complete reconstruction will be the mirror-image of the object, geometrically. It will now be seen how medium I reconstructs the mirror-image acoustical impedance to the object, as well.

Figure 2:
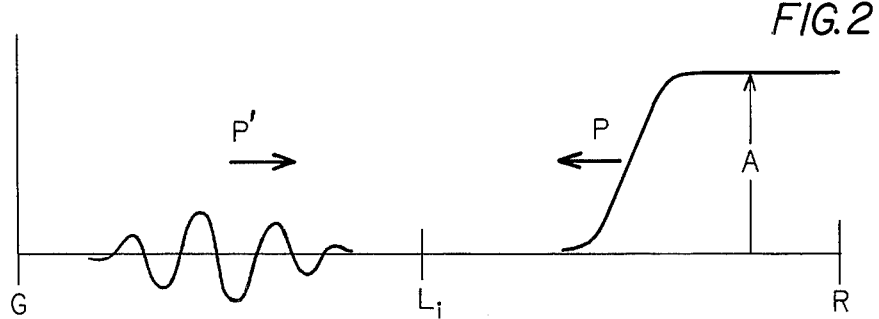
FIG. 2 shows the two types of pulse waveforms utilized in the method, namely P and P', with appropriate orientation just prior to interaction: P' is moving to the right and P is moving to the left. They will interact in L. Here, subscripts are left off, but pulses and layers will be distinguished later by subscripts referring to a step in the method.
Figures 3A, 3B, 3C, 3D, 4:
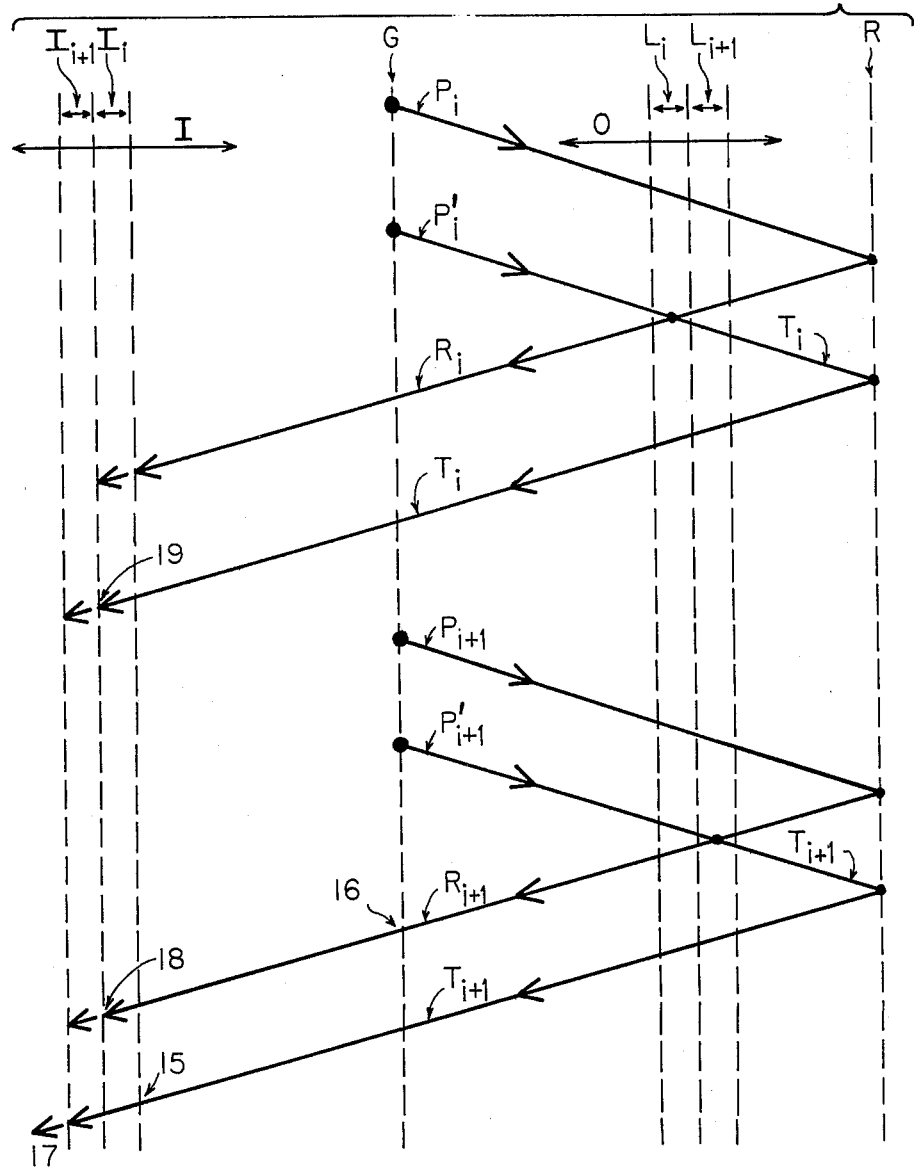
FIGS. 3a, 3b, 3c and 3d show cross sections of the individual powder particle mechanisms used to process ultrasonic pulses and waves, with their four operating states, respectively. There are two types of capsular-shaped particles, but since they are nearly identical in shape, only the first type, aI, is shown.
FIG. 4 is the "wave diagram" showing the motions of all pulses used to extract absorptivity and refractivity information from the object between times $(i-1)\Delta T$ and $(i+1)\Delta T$. Pulses $P_i$ and $P_i'$, for example, have the waveforms of P and P', respectively in FIG. 2.

At the first step of the process, $R_o$ is discarded as generated in $L_o$ by $P_o$ and $P_o'$ ($L_o$ being homogeneous) but $T_o$ is recorded in $I_1$ as velocity-information (the frequency-shift of $T_o$ being due to penetration into $L_1$ and $P_o$ there). The following are the stages of the $(i+1)$-st iteration of the recursion: Firstly, a pulse $P_i$ (with waveform as P, FIG. 2) is generated in G, (FIGS. 1 and 4) and travels through the object O (the composite of layers $L_1, L_2, \ldots$ in FIG. 1) into reversal medium R, where its direction of propagation is exactly and instantaneously reversed at all points of R upon activation of R by the RF-field of step b, above. This "reversal" is more properly called "conjugation," and will be so designated hereafter. A conjugated wave has the property that following the instant of conjugation, it exactly retraces its path followed up to that instant backwards, not as if reflected, but without its waveform being turned around; that is, the head of the wave-train becomes the tail and the tail becomes the head when moving in reverse. Thus, pulse $P_i$, after conjugation, will eventually arrive back at object layer $L_i$ with the same wavefront-geometry it had on passing through $L_i$ in the forward direction, but it will now be travelling in the reverse direction, back toward the generator. Due to the high RF-field of activation, R behaves in an all-or-none manner in expansion of stimulated type $aI$ micromechanisms, and variations of amplitude due to absorption in O are smoothed out, but frequency-information is not distorted. Secondly, $P_i'$ is generated in G at such a time (FIG. 4) that it interacts with $P_i$ coming back in $L_i$. Absorptivity at layer $L_i$ is determined by intensities of $P_i'$ at $L_i$ and at $L_{i-1}$, or, equivalently, by the intensity $J_i$ of $P_i'$ at $L_i$ and the intensity of $P_{i-1}'$ at $L_{i-1}$ (since $P_i'$ and $P_{i-1}'$ agree in intensity at $L_{i-1}$). As can be seen from the definition of absorptivity, $a$, as $J(t+dt) = J(t)e^{adt}$, the approximate formula for absorptivity $a_i$ at $L_i$ is:

$$a_i \simeq (J_{i-1} - J_i)/J_{i-1}\Delta T)$$

where $\Delta T$ is the travel-time through $L_i$ (actually equal for all layers). Still at the layer of intersection, $L_i$, pulses $P_i$ and $P_i'$ there generate pulses $R_i$ and $T_i$, thirdly, by "Doppler-type" nonlinear interaction in $L_i$ (at point 14 in FIG. 4): The frequency of $P_i'$ as it moves through $P_i$ into the "transmitted" $T_i$ moving in the same direction, is raised by the moving front of the much larger amplitude "tidal" pulse $P_i$, while at the same time, the amplitude of $P_i$ is increased by a reflected part of $P_i'$ due to the nonlinear effect of increased density in the front of $P_i$. It turns out that the increased amplitude of $R_i$ over $P_i$ at $L_i$ is proportional to the amplitude of $P_i'$ at $L_i$ (the amplitude of a tidal pulse, like P in FIG. 2, does not decrease appreciably as it propagates) and that the velocity $v_i$ of ultrasound of freqency $f_o$ in layer $L_i$ is given by:

$$v_i = C(f_i - f_o)/(Af_o)$$

where $f_i$ is the raised frequency due to $P_i$ which has amplitude A, and where C is a proportionality constant depending on dimensions or units and on $f_i$ to some extent, but for small excursions of $f_i$ in relation to $f_i - f_o$ (less than 10%, say) this formula holds in sufficiently good approximation for the purposes of reconstruction. Fourthly, $T_i$ passes on through the object to R, where it is conjugated, and then follows its path back through the object, G, $I_o$, $I_1, \ldots, I_{i-1}$ to image layer $I_i$ (FIG. 1, see also FIG. 4). At $I_i$, $T_i$ has a wave-front geometry which is the mirror-image of that which it had in $L_i$, since each image layer $I_j$ ($j=1, \ldots, i$), has been constructed by preceding iterations of these steps so as to have the mirror-image refractivity (velocity) of corresponding object layers $L_j$ with respect to the plane of G as the mirror, and since the $I_j$ are geometrically the mirror-images of the $L_j$ ($j=1, \ldots, i$). Thus $T_i$ arrives at the beginning of (not yet reconstructed) layer $I_{i+1}$ with frequency $f_i$, higher than the fundamental frequency of generation $f_o$, in proportion to the propagation velocity in mirror-image points of $L_i$. Fifthly layer $I_{i+1}$ is activated at this time (15, FIG. 4) by high RF- and magnetic fields as in $d$ so that the increase of frequency mentioned in $d$, corresponding to $f_i - f_o$ here, is recorded by type $nf$ micromechanisms in $I_{i+1}$, and this information can later be recalled as intrinsic velocity of propagation which, at each point, will be equal to that of the mirror-image point in $L_{i+1}$ (it being understood that a certain amount of error must be introduced). As preconditions for recursion, it should be noted at this stage that $R_i$ has been recorded in $I_i$ in terms of amplification capacity proportional to mirror-image absorptivity in $L_i$ and of absorptivity in $I_i$ proportional to $J_i/J_{i-1}$ in the state of recall ($e$). Sixthly, $I$ is recompressed and reactivated with momentary high RF-field as in $e$ so recorded type $aI$ expand, and then placed under lower RF- and magnetic fields, returning type $aI$ to $f$ (16, FIG. 4). Seventhly, pulse $R_{i+1}$ is generated (possibly before step six) in $L_{i+1}$ and travels back through object (FIGS. 1 and 4) to $I$ after step seven, where it is then amplified by layers $I_1, \ldots, I_i$ under low magnetic field and low RF-field as in $f$, with amplification which is mirror-image to attenuation in $L_i, \ldots, L_1$ and with velocity of propagation also mirror-image to that in $L_i, \ldots, L_1$, as explained above, and, with concurrent attenuation proportional to $J_i$, as will be explained; thus $R_{i+1}$ arrives at $I_{i+1}$ with mirror-image waveform and wave-front geometry to those it had in $L_i$, and, in addition, with intensity proportional to the mirror image of its intensity in $L_{i+1}$ divided by the mirror image of the intensity of $R_i$ in $L_i$; namely, proportional to $J_{i+1}/J_i$. This proportionality constant will be discussed later. Thus $R_{i+1}$ arrives at $I_{i+1}$ with mirror-image intensity proportional to the ratio of $J_{i+1}$ over $J_i$. The above constant is so adjusted, by empirical determination of appropriate activating RF-field intensity (depending on the batch of type $aI$ used in a rather unpredictable but homogeneous manner) that $R_{i+1}$ leaves compressed a fraction of the population-density of micromechanisms of type $aI$ in $I_{i+1}$ equal to one minus this ratio $(J_{i+1}/J_i)$ of intensities; in other words, expands a fraction equal to $(J_{i+1}/J_i)$. It can be seen by elementary algebra that the fraction unexpanded (unrecorded) is proportional to the absorptivity $_xa_i$ in layer $L_i$ according to the above formula for $a_i$. Note that the fraction unrecording at this stage is precisely that required to amplify $T_{i+1}$ at a later stage when in state $f$ (unexpanded micromechanisms are more sensitive to activation by a lower RF-field than expanded, as mentioned above, thus only the unrecorded ones will expand and thereby amplify at that stage; the recorded ones will remain compressed and thus not attenuate as in the present stage). Moreover, while $R_{i+1}$ is passing through $I_{i+1}$, the RF-field of $c$ is momentarily applied, without magnetic field, so that only type $aI$ micromechanisms are activated to record the intensity, but $R_{i+1}$ moves with mirror-image velocity to that it had in $L_{i+1}$, since this information was previously stored by $T_i$ in $I_{i+1}$ and recalled at 15. At time $(i+1)\Delta T$, all activation is shut off, thus allowing $R_{i+1}$ to record in I beyond $I_i$ to a depth $v_{i+1}\Delta T$, which can easily be seen to be the thickness of $L_{i+1}$, hence the thickness of $I_{i+1}$, at a given point. Here, it is seen that the lengths of $R_i, T_i, R_{i+1}$ and $T_{i+1}$ are not particularly critical, since the timing of activations determines thicknesses, but that pulse-lengths should not be much longer than minimum layer thickness, to avoid multiple exposure. At this point (17, FIG. 4) $L_{i+1}$ has been fully recorded. To aid the implementer of the above recursive process, certain points will now be illustrated by way of the above mentioned example employing 1.5 MHz ultrasound, but are in no way intended to restrict the scope of the invention thereby illustrated. Firstly, a wide range of sound intensity may be used, depending on the opacity (transmisivity) of the object to be imaged by the process. For biological preparations containing mostly soft tissue, with relatively little bone thickness, intensities of P' were typically taken between 10 and 100 W/cm² (for living tissue, 10 W/cm² is about maximum undamaging intensity) The intensity of P should be at least ten times as great, as a rule of thumb, and as far as we can determine, a 100 W/cm² "tidal" pulse of the form P also does not damage living tissue. However, the invention is envisaged to apply to non-destructive testing, and possibly at lower frequencies to seismographic structure determination, as well as many other applications involving large proportions of solid to liquid in the object. In such cases, the tidal pulses $P_i$ should be as large as possible, preferably much greater than a factor of 10 over $P_i'$ in intensity, as for example might be produced by placed charges for mantle structure determinations or by sharp blows struck by an electrically driven hammer in the testing of metal or plastic parts. For biological imaging, it was found that layers could be as thin as 1.5–2 wavelengths of the sound used, or about 1 mm for 1.5 MHz, and that distortion errors in the image became noticeable between 15 and 20 layers at worst, when the samples were highly multiply scattering, as with many bones, liquid pockets and vessels. Above 20 layers, local relationships are still well preserved, and good topological integrity is maintained globally, that is for example, there are no discontinuities in the transformation from object to image out to 30 to 50 layers. Although resolution is about the same, this is a considerable improvement over holographic means which are good to one or at most two partially reflecting layers, beyond which nothing can be determined. It should be mentioned, however, that holographic means could be utilized in place of R as a conjugator, an immediate property of holographic reconstruction. The possibility of using holographic means to reconstruct thicker layers, in place of the testing pulses, P and P', has been considered theoretically, and, aside from being actually more complicated than the present invention, can be shown to be much more sensitive to slight movements (thermal drifts, vibrations, etc.) of the holograms and of the image and object (movements of the latter in the case of biological preparations are a real problem, due to heartbeat, pulsatile blood flow, muscle contractions, etc.). Regarding R, metallic coated mylar, as used in wound capacitors for example, was found excellent for surface 4 of the waveguide about R. It passes 1.5 MHz ultrasound with very little reflection. Reflection due to a piezoelectric disc as G can be significant, particularly where intensity of P' is minimum for processing by the micromechanisms. Therefore, a relatively translucent transducer was constructed of multiple layers of metallic coated mylar, with alternate layers connected to the (higher) voltage source, and acting like capacitance microphones in-phase at wavelength separation, but this is not essential to the invention by any means. A good pressure regulation device for 3 in FIG. 1 was constructed in the obvious manner with a solenoid actuator connected to a sound-absorbing pressure-piston 5, which is a diaphragm closing off one side of a chamber connected hydraulically to the chamber containing medium I. This had a response time of 1.2 millisecond, allowing the timing circuitry to be described to initiate one recursive step every 2 milliseconds. Better pressure transducers of up to about 5 microseconds would allow an image of 20 layers to be constructed in 100 microseconds, for 1.5 MHz sound. A relay was used to control the higher current of the solenoid. Again by way of illustration only, the timing circuitry (6, FIG. 1) will now be described for the particular application with 1.5 MHz ultrasound. Given $2^N$ as the maximum number of layers desired (say, 64), two ring-counters with $N$ bit-positions, each, are connected as follows so that nine output pulses, called triggering signals, are separated by fixed times corresponding to the actuation of $G$ and the activations necessary in the recursive process. The high-order bit of the first ring-counter is connected to advance the second ring-counter by one (low-order) bit, or "count." Thus, when the first had counted to $2^N$, it advanced the second by one count (corresponding to the propagation-time through a layer, $\Delta T$). Each time the second ring-counter reaches the first count $(T + \Delta T$ seconds later than the previous time, where $T$ is the cycle-time of the first ring-counter, $2^N \Delta T$) as determined by "and-ing" the counts of both ring-counters, the first of the nine triggering signals is sent through amplifier (8, FIG. 1) to $G$, initiating a pulse of type $P$ (FIG. 2). Each time the first ring-counter reaches its last count (a ring-counter cycles, due to one of its stages being a multi-stable flip-flop) the second triggering signal commands pulse generator 7, (FIG. 1) to initiate a pulse of type $P'$. Therefore, the first time through, with the ring-counters starting off together, $P_o$ and $P_o'$ are at the maximum time-separation, $T = 2^N \Delta T$, the travel-time through the object, and intercept at the beginning of $L_1$, that is, the first point reached on the object. As the number of recursions increases, the coincidence of counts occurs incrementally ($\Delta T$) closer to the last count of the first ring-counter, hence $P_i$ and $P_i'$ become closer together, until at the end of the process, they intersect in the last layer, $L_N$ (the highest order bit signal of the second ring-counter shuts off the local oscillator driving the first ring-counter). At the $i$-th repetition, for example, the third of the 9 output signals from the combined ring-counters set off the conjugator, $R$, at a delay from the first signal just equal to the travel-time of $P_i$ through the object to when $P_i$ is just inside $R$ (this can be estimated, or in case of doubt, measured by Brillioun scattering of light through the transparent coupling bath around the object). $R$ can be made fairly thick, so that this delay is not critical. Depending on the length of the apparatus in an obvious way, the next step in the recursive process requiring a timing pulse is usually the arrival of $T_i$ in $R$. This pulse is created by the first ring-counter at a delay also equal to the above travel-time of $P_i$ from its last count (creating $P_i'$), and is thus the fourth of the 9 outputs, triggering the conjugation of $T_i$ in $R$. The fifth event is the arrival of $R_i$ at $I$, and the fifth output signal activates $I$ with RF- and magnetic field, causing amplification of $R_i$ in $I$. This is also a fixed delay from the generationtime of $P_i$ in $G$, as kept track of by the second ring-counter. The sixth triggering signal removes magnetic field as $R_i$ reaches $I_i$, so that its absorptivity-information can be recorded in $I_i$, and this signal is one count ($\Delta T$) later than the fifth. The seventh triggering signal turns off the RF-field as $R_i$ reaches $I_{i+1}$ (and, optionally, the magnetic field) at one more count of the first ring-counter. There is an optional triggering signal that could turn the magnetic field back on as $T_i$ enters $I$, if this should turn out to be necessary to additionally protect type $nf$ micromechanisms from false expansion (above what the lack of RF-field does). The eighth triggering signal turns on the RF-field as $T_i$ reaches $I_{i+1}$ as well as the higher magnetic field necessary for recording of velocity-information of $T_i$ in $I_{i+1}$. Finally, the nineth triggering pulse turns off all fields, so $T_i$ will not damage any deeper micromechanisms of $I$, until the next iteration of the recursive process, when $R_{i+1}$ arrives. Note that the time-course followed here overlaps the explanation of the recursive process, before, but this should not cause confusion, as $R_{i+1}$ is handled in the same manner as $R_i$.

With the preceding illustration, there are some fine points implicit in the recursive process which can now be clarified. Firstly, since no velocity-information is available in $I_{i+1}$ at the time $T_i$ enters it, $T_i$ will only penetrate $I$ beyond $I_i$ to a depth equal to $\Delta T$ times the nominal velocity of propagation in (unrecorded) $I$, an uniform thickness, whereas the real thickness of $L_{i+1}$ varies. However, when $R_{i+1}$ comes through, it is carried to this real thickness by the already recorded velocity information. In order to avoid the slight reflections due to thin layers of discrepancy in index of refraction, what is done in practice is to allow $T_i$ to carry on a little farther (due to the finite fall-time of the field shut-off by the nineth triggering pulse). There may be some slight overlap of the recording of $T_i$ and $T_{i+1}$, but the second cannot begin recording, actually, until the first is finished, due to the permanent nature of the recording, and thus there is no double recording and no unrecorded volumes. Secondly, since the recording of velocity in type $nf$ micromechanisms cannot be made perfectly independent of intensity, it may improve resolution and accuracy in more difficult applications if the intensity of $T_i$ is normalized as it passes back through $G$ (by a nearly all-or-none responding, saturated $R$). Thirdly, in some applications, it may be necessary to have three distinct intensities of RF-field, as implied by steps $c, d$ and $e$ above, called RF-field, higher RF-field and lower RF-field, respectively. However, at 1.5 MHz it was found that the lower RF-field could actually be equal to the RF-field, with only the presence of the lower magnetic field being sufficient to select between the amplifying state $f$ and the recording state $c$, respectively. The inventor does not wish to restrict the invention to only two intensities of RF, because in certain applications, particularly low ultrasonic intensities, it may be necessary to insure that type $aI$ micromechanisms do not accidentally record while in amplification. As mentioned above, a somewhat lower intensity RF-field than that used in $c$ to record will still cause type $aI$ shells to expand, even though they have not been expanded in the recording process, due to the lower magnetic field in the amplifying state $f$ which apparently tends to keep the magnetic particles in contact as the adhesive begins to expand, beyond the point in state $c$ without magnetic field, and thus heats the adhesive to a higher temperature by the lower RF-field than by the RF-field alone. Fourthly, it was to be explained in the eighth stage of the recursive process how $R_{i+1}$ could reach $I_{i+1}$ with an intensity equal to the intensity $J_{i+1}$ it had in $L_{i+1}$ divided by the intensity of $R_i$ in $L_i$ (that is, at the $i+1$-st repetition of the recursive process). This is due to the fact that in each of the preceding layers $I_j, j = 1, \ldots, i$, the fraction of expanded (recorded) type $aI$ is proportional to $J_j/J_{j-1}$. Their degree of scattering is such that expanded $aI$ will attenuate by this factor in $I_j$, which has transmission time $\Delta T$. Now $I_o$ is not used to record, hence its attenuation is uniform and almost negligible. Therefore, the fraction expanded in the recording of $I_1$ is just $J_1$ (there being no variation in $J_o$). Hence, the combined attenuation of $I_o, \ldots, I_i$ is $$(J_i/J_{i-1})(J_{i-1}/J_{i-2}) \ldots (J_2/J_1)(J_1) = J_i,$$

Thus $R_{i+1}$ arrives at the beginning surface of layer $I_{i+1}$ attenuated by $J_i$. Since $R_{i+1}$ has also been amplified concurrently with this attenuation, such that without this attenuation it would arrive at $I_{i+1}$ with mirror-image intensity to $J_{i+1}$, in $L_{i+1}$ the combined effect of both amplification and attenuation is that it arrives at $I_{i+1}$ with mirror-image geometry and intensity $(J_{i+1}/J_i)$; It can now be seen how the operating parameters of type $aI$ mentioned earlier must be adjusted. The sensitivity of type $aI$ is to be such that the fraction thereby expanded in $I_{i+1}$ during stimulation/time-interval $[i\Delta T, (i+1)\Delta T]$ must be $(J_{i+1}/J_i)$. Of course, this is an expectation value, in view of the probabilistic nature of expansion mentioned earlier. The fraction left unexpanded by $R_{i+1}$ in $I_{i+1}$ must then be one minus $(J_{i+1}/J_i)$. It can now be seen that the proportionality constant mentioned above between absorptivity $a_i$ and unexpanded fraction must be adjusted to $(1/\Delta T)$.

Absorptivity in the above sense should not be confused with the attenuation coefficient.

The patentee has found several alternative methods for processing R- and T- type pulses using type $nf$ and $aI$ or similar, but the above recursive process, or slight variations thereupon, have been found the simplest and easiest to implement and thus are considered the best mode of practicing the invention.

I claim:

1. A process for the multiple-layer, layer-by-layer reconstruction of the internal structure of a solid, liquid or solid-liquid object comprising: exciting said object with ultrasonic waves during a time interval where $\Delta T$ determines thickness of an $i$-th object layer ($L_i$) as the time taken for said waves to pass through said layer, at an $i$-th step of said process, depending recursively on identical steps numbered $1, 2, \ldots i-1$ having been performed previously, such that a coherent, monochromatic wave-pulse pair ($P_i, P_i'$) generated in standard ultrasonic generating means outside said object pass simultaneously through and define said $i$-th object layer during said time interval and generate two additional pulses in said $i$-th layer: one ($R_i$) transmitting information about absorptivity in said $i$-th layer, and the second ($T_i$) transmitting information about propagation velocity or refractivity in said $i$-th layer, said wave and pulse ($P_iP_i'$) arriving at said $i$-th object layer after the pulse ($P_i$) has been conjugated in a conjugator operated as a reversal medium which returns the conjugate of an incident wave, and in which said additional two pulses activate an image medium by having particles responsive to the activation and further responsive to the additional two pulses to constitute a recording means in the image medium wherein said absorptivity and refractivity information are used to reconstruct the acoustic impedance three dimensional analog of the object, said image medium, reversal medium, generating means and object being sonically coupled to transmit and transfer said ultrasonic waves and pulses between said media, generating means and object, said image media being coupled to a magnet coil and a microwave source with means for energizing said coil and source to activate said media for recording.

2. Process according to claim 1, wherein said image medium is used to reconstruct the acoustic impedance properties, absorptivity and refractivity, in image layers contained in said image medium ($I_1, I_2, \ldots$) which are the mirror-images, geometrically and acoustically, of corresponding said object layers ($L_1, L_2, \ldots$) with respect to the plane in which said generator (G) lies; said correspondence being one-to-one between said image and object layers such that the $i$-th image layer ($I_i$) reconstructed using absorptivity and refractivity information transmitted by said two additional pulses of said $i$-th step, is the geometrical and acoustic mirror-image of the said $i$-th ($L_i$) object layer with respect to the plane in which said generator lies.

3. Process further according to claim 1 wherein said $i$-th step depends on preceding and identically defined steps numbered $1, 2, \ldots i-1$ having been performed previously recursively, and is defined as follows:

firstly, generating said wave pulse outside said object in said generator, and passing through said object to the beginning of said $i$-th layer;

secondly, activating said object during said time interval $|i\Delta T, (i+1)\Delta T|$ that said wave-pulse pair generates said two additional pulses ($R_i, T_i$);

thirdly, processing first said additional pulse ($R_i$) on passing through image layers number $1, 2, \ldots$ and $i-1$ which have been properly prepared previously so that its said information transmitted about absorptivity at each point in said $i$-th object layer is then recorded as an amplification capacity at the corresponding mirror-image point in the $i$-th image layer;

fourthly, processing second said additional pulse ($T_i$) on passing through image layers number $1, 2, \ldots$ and $i-1$ which have been properly prepared previously so that its said information transmitted about refractivity at each point in said $i$-th object layer is then recorded as velocity of propagation intrinsic at that point and equal to velocity of propagation at the corresponding mirror-image point in the $i$-th image layer.

4. Process according to claim 3 wherein said recorded amplification capacity at each point of said image layers is made equal to the attenuation coefficient, at the corresponding mirror-image point of said object; and that said recorded velocity of propagation at each point of said image medium being equal to that at mirror-image object points, in combination with said equality of amplification factor and attenuation coefficient, such that the time-course of a wave arising in said object can be nearly exactly reconstructed in said image medium; said time-course reconstruction including mirror-image wave-front geometry, and wave amplitude.

5. Process further according to claim 1 wherein said object activation and method of processing said additional two pulses ($R_i, T_i$) are defined and related as follows: said wave ($P_i'$) is generated as said outside object at an instant of time chosen so that said pulse ($P_i$) has already passed once through the entire said object into said conjugator, where its direction of propagation has been reversed, and thus it retraces exactly its path back through said object up to said $i$-th object layer ($L_i$); wherein said wave and said pulse can then interact non-linearly to generate said additional two pulses ($R_i, T_i$); said non-linear interaction comprising said activation method.

6. Process according to claim 1 utilizing said image medium, hereafter termed I, with the following image layer activation means and recording and recall properties:
  firstly activating said I by an externally applied, alternating electromagnetic field of microwave frequency such that I alters said amplification capacity at each of its points proportionally to the intensity of an ultrasonic wave which is passing through I at the time of application of said field according to the formula $(J_{i-1} - J_i)/(J_{i-1}\Delta T)$ wherein $J_{i-1}$ is the intensity of said wave $(R_{i-1})$ in the preceding step $i-1$ as it reaches the beginning of the $i-1$-st object layer, and wherein $J_i$ is the intensity of said wave $R_i$ in step $i$ as it reaches the beginning of the $i$-th object layer;
  further differently activating said I by said electromagnetic field in combination with an externally applied, constant magnetic field ($e$), for the duration of said activation, such that I alters its velocity of propagation of said ultrasonic waves in proportion to the frequency difference between the fundamental frequency of said ultrasonic wave, $f_i$, and the frequency of ultrasound as originally generated in said generator according to the formula $C(f_i - f_o) / (Af_o)$ wherein C is approximately constant depending on dimensions or units and wherein A is the amplitude of said pulse as it reaches the beginning of the $i$-th object layer;
  said information transmitted about absorptivity which is recorded after passage of said first of additional pulses of just preceding said step $i-1$ ($R_{i-1}$) and at the arrival of said second of additional pulses ($T_i$) of said step $i$ at said $i$-th image layer will be destroyed by subsequent passage of another ultrasonic pulse or wave, but can be recalled by a momentary increase of ambient medium pressure, called reactivation, followed by application externally of a microwave electromagnetic alternating field of somewhat lesser intensity than said electromagnetic field, in combination with a second magnetic field as distinguished from the said constant magnetic field; the former said electromagnetic field being hereafter called higher intensity RF-field and the latter electromagnetic field of lesser intensity being hereafter called lower intensity RF-field;
  activating said I by the application externally of an electromagnetic field of greater or equal intensity to said higher intensity RF-field, following said alteration of intrinsic amplification capacity, such that at points which have been so activated and prepared, I has intrinsic absorptivity at each of its points in proportion to the intensity of said ultrasonic wave passing through said points at the time of activation;
  said electromagnetic field of greater or equal intensity, as well as said lower intensity RF-field, being adjusted in their intensities relative to said higher intensity RF-field empirically as need for a particular image medium.

7. Process as in claim 1 wherein said conjugator (R) operates at the precise instant of time at which said conjugator is activated by the application of an alternating electromagnetic field of microwave frequency the direction of propagation of any ultrasonic wave or pulse which happens to be passing through the conjugator will be nearly exactly reversed, so that said wave or pulse retraces its path in reverse.

8. The process further as in claim 6 wherein said additional two pulses ($R_i$, $T_i$) are processed, is comprised of a repetition of the following step depending recursively on identical steps 1,2, ..., $i-1$ preceding:
  said pulse ($P_i$) is generated in said generator (G) and passes through said object (O) into said conjugator (R), wherein its direction of propagation is reversed;
  next, said pulse collides in the said $i$-th object layer ($L_i$) similarly generated in said generator, such that by non-linear interaction of pulse and wave, said two additional pulses ($R_i$, $T_i$) are generated;
  next, second of said additional two pulses ($T_i$) then passes on through said object into said conjugator, wherein it is reversed and passes back through said object and generator, and the first $i-1$ image layers, $I_1, I_2, \ldots, I_{i-1}$, up to said $i$-th image layer, $I_i$;
  next, said $i$ image layers $I_1, \ldots, I_i$ being under activation by said RF-field of lower intensity, together with said second magnetic field,
  said second of two additional pulses ($T_i$) arrives at the $(i+1)$-st image layer $(I_{i+1})$, 19 with a wavefront geometry which is the mirror-image of that which said pulse had when it was at the corresponding $(i+1)$-st object layer $(L_{i+1})$, and with mirror image amplitude (A);
  at which moment (19), said $(i+1)$-st image layer is then activated by said higher intensity RF-field of higher intensity, together with said constant magnetic field, so that said frequency difference $(f_i + f_o)$ is recorded in said $(i+1)$-st image layer as an intrinsic velocity of propagation equal at each point to that of the corresponding mirror-image point in the $(i+1)$-st object layer, said frequency being recorded permanently under combination of fields applied externally by subsequent steps of said process;
  next, said $i-1$ image layers $I_1, \ldots, I_{i-1}$ having been prepared for activation previously by passage of first said additional pulse ($R_i$) and according to steps 1,2, ..., $i-1$ in such a manner that said absorptivity of each of said $i-1$ image layers is proportional to the ratio of intensities of first pulse ($R_j$) in step number $j$ over preceding first pulse ($R_{j-1}$) of step $j-1$, for $j$ equal to 1, 2, ... and $i-1$,
  said first pulse ($R_{i+1}$) of said step $i+1$, reaches said $(i+1)$-st image layer, with intensity proportional at each point to its intensity at corresponding mirror-image points divided by the intensity of preceding said first pulse ($R_i$);
  at which moment (18), said $(i+1)$-st image layer is put under said higher electromagnetic field, but not under said magnetic field ($e$);
  and said newly arrived first pulse ($R_{i+1}$) has its absorptivity-information recorded by means of said higher intensity electromagnetic field, to be recalled in subsequent iteration 15 of said recursion by means of said reactivation, as an amplification capacity equal to absorptivity at corresponding mirror-image points of said object to points of said $(i+1)$-st image layer, completing said recursive step as $i$-th iteration;
  said above recursive process starting at the zero-th iteration with said image medium having the same acoustical impedance, namely homogeneous, as the liquid bath in which said object is contained and coupled to said generator and said coupling apparatus (R), and said first pulse ($R_o$) as generated externally to said object in said liquid bath ($L_o$) by interaction of said pulse ($P_o$) and said wave ($P_o'$) is discarded, whereas said second pulse ($T_o$), passing on through said object to said conjugator, where it is reversed, and passing back through said object and generator, and into said image medium (I) to a position which is the mirror-image with respect to said generator of its position when just touching said object, is recorded by activation of said higher intensity electromagnetic field and said magnetic field (e) during time $\Delta T$ as first image layer ($I_1$).

9. Process as in claim 6 wherein the reconstruction medium, otherwise called image medium, I, consists of a uniform mixture, that is, homogeneous mixture of two types, *a*I and *nf*, of microscopic mechanisms in a liquid vehicle wherein said type *a*I is prepared for operation by a temporary pressure greater than that equilibrium pressure under which the mechanisms perform their functions, which pressure conveyed to said mechanism by said liquid vehicle, while at the same time an electromagnetic field of sufficient, intensity and frequency is applied to said mechanism, by means (9) external to said I, to heat an adhesive coating (4) on the inner surface of said mechanism's shell (3) above the melting point of said adhesive, while said greater-than-equilibrium pressure compresses said mechanism into a compressed state (3*b*) in which opposite sides of its said shell are lightly touching; said shell having less volume in said compressed state than in its original, uncompressed state (3*a*);

said type *a*I is further prepared for operation by reduction of said electromagnetic field until such a time as adhesive temperature drops below said melting point, and then reduction of said pressure to said equilibrium value, said electromagnetic field being of such an intensity as to hold said adhesive temperature just below said melting point, all the while said reduction of electromagnetic field is taking place a constant magnetic field being applied to orient magnetic, electrically conducting particles in said adhesive and to keep them in electrical contact, and said equilibrium pressure being such that said shell remains in said compressed state;

said type *a*I is activated for the function of expanding in a stimulating ultrasonic wave within a time not greater than one-quarter period from pressure maximum, otherwise called over-pressure, of said ultrasonic wave by the application of a reduced electromagnetic field (*b*), otherwise called RF-field, which heats said adhesive in said prepared compressed mechanism to a temperature just below said melting point;

under said RF-field, said micromechanism has its said shell slightly compressed by said over-pressure of said stimulating ultrasonic wave so that said conducting particles are pressed into better electrical contact, that is, reducing the resistivity of the said adhesive and thus increasing its temperature in said RF-field above said melting point, allowing said shell to expand to its expanded, spherical, state (3*d*), with a probability closely proportional to intensity of said stimulating ultrasound within the dynamic range of normal, operating sound intensities for said type *a*I mechanisms, said expansion being called recording;

whereas under a magnetic field of strength lower than that of said constant magnetic field and under an electromagnetic field of same frequency but intensity equal to or somewhat lower than said electromagnetic field, being called lower intensity electromagnetic field, said mechanism having its shell slightly compressed by said overpressure will expand to its spherical state (3*d*) with a probability closely proportional to stimulating sound intensity, within said dynamic range, said expansion being called amplifying if said mechanism is in said medium I or conjugating if said mechanism is in said coupling apparatus (R);

said type *a*I mechanism is returned to its compressed state by recompression with said greater-than-equilibrium pressure, tacking broken bonds of said adhesive back together, and then reactivated by temporary application of said higher intensity electromagnetic field so that shells previously expanded will again expand (*e*);

said recording and amplifying expansions in said I being distinguished subsequently in the manner in which respective shells re-expand after said recompression and reactivation, as follows:

said adhesive will not have its electrical resistivity decreased by said amplifying expansion, so that unrecorded shells, if amplifying in said I, can be recompressed and reactivated without difference from their original, unexpanded and unrecorded state, whereas said recording expansions decrease said adhesive resistivity by disorienting said magnetic particles, or otherwise separating said magnetic particles, due to adhesive deformation and without the orienting and aggregating effect of said magnetic field, so that after said recompression and reactivation, said recorded shells re-expand;

said type *a*I mechanisms in said liquid vehicle are able to amplify, i.e. conjugate, a stimulating ultrasonic wave by increasing local pressure in their containing medium upon stimulation by smaller increase of said over-pressure due to said increase of volume in expansion.

10. Process as in claim 9 wherein:

said *nf* structure is a shell, coated on its inner side with said adhesive, the same as said type *a*I with the addition of a coating of magnetic particles on the outer side of said shell, held to the shell and held together by the same elastic material of which said shell is composed; same said preparation as said type *a*I mechanisms, before activation; under said activation, in addition to said RF-field as for said type *a*I, with said constant magnetic field, said coating of magnetic particles increases the ability of said shell to resonate (Q) under the small compressions and rarefactions of a stimulating ultrasonic wave, and said shell under said activation has a resonant frequency equal to the generation-frequency $f_o$ of said generator (G), so that the probability that said type *nf* will expand from its said activated state in the presence of said ultrasonic wave is very much decreased by a slight increase in frequency of said ultrasound over $f_o$;

once so expanded to its spherical state, otherwise called expanded state, said type *nf* cannot be returned to its unexpanded state except by said preparation, called permanent erasure.

11. Process as in claim 9 wherein the liquid vehicle has the following properties:

said liquid vehicle has the same acoustical impedance as both type $aI$ and type $nf$ mechanisms in their respective said compressed states, that is, mixtures of said mechanisms with said liquid vehicle in said prepared but unrecorded states are acoustically transparent and homogeneous with respect to acoustical properties;

said type $aI$ mechanisms have lower density in said expanded state than the density of said liquid vehicle, hence said type $aI$ mechanisms are able to scatter, or otherwise termed absorb, or otherwise termed attenuate, said ultrasonic waves;

said type $nf$ mechanisms have bulk modulus of elasticity in said liquid vehicle when under said lower magnetic field or said constant magnetic field lower when expanded than bulk modulus of elasticity when compressed;

said liquid vehicle, when mixed with said powders of type $aI$ mechanisms and $nf$ mechanisms as in said image medium, and when said mechanisms are all compressed to said compressed states, has acoustical impedance equal to that of said liquid bath;

and said liquid vehicle, when all mechanisms are in said compressed states, has intrinsic velocity of propagation for said untrasound just greater than the maximum velocity of propagation of said untrasound in any object which it is desired to image, otherwise termed, reconstruct the image thereof.

* * * * *